(12) United States Patent
Deviere et al.

(10) Patent No.: US 12,133,986 B2
(45) Date of Patent: Nov. 5, 2024

(54) TISSUE ANCHORING ASSEMBLY

(71) Applicant: Université Libre de Bruxelles, Brussels (BE)

(72) Inventors: Jacques Deviere, Bornival (BE); Antoine Nonclercq, Brussels (BE); Adrien Debelle, Brussels (BE); Laurent Lonys, Brussels (BE); Fabrizio Giannotta, Vaux-sous-Chevremont (BE); François Huberland, Ixelles (BE)

(73) Assignee: Université Libre de Bruxelles, Brussels (BE)

( * ) Notice: Subject to any disclaimer, the term of this patent is extended or adjusted under 35 U.S.C. 154(b) by 684 days.

(21) Appl. No.: 17/414,746

(22) PCT Filed: Dec. 11, 2019

(86) PCT No.: PCT/EP2019/084742
§ 371 (c)(1),
(2) Date: Jun. 16, 2021

(87) PCT Pub. No.: WO2020/126770
PCT Pub. Date: Jun. 25, 2020

(65) Prior Publication Data
US 2022/0072320 A1    Mar. 10, 2022

(30) Foreign Application Priority Data

Dec. 18, 2018   (EP) .................................... 18213753

(51) Int. Cl.
*A61N 1/375*     (2006.01)
(52) U.S. Cl.
CPC ....... *A61N 1/37518* (2017.08); *A61N 1/3754* (2013.01)

(58) Field of Classification Search
None
See application file for complete search history.

(56) References Cited

U.S. PATENT DOCUMENTS

| | | |
|---|---|---|
| 3,976,082 A | 8/1976 | Schmitt |
| 4,066,085 A | 1/1978 | Hess |

(Continued)

FOREIGN PATENT DOCUMENTS

| | | | |
|---|---|---|---|
| DE | 2133304 A1 | 1/1973 | |
| EP | 4967 A2 | 10/1979 | |

(Continued)

OTHER PUBLICATIONS

MatWeb. https://www.matweb.com/search/DataSheet.aspx?MatGUID=cbe7a469897a47eda563816c86a73520. Accessed Feb. 2, 2024 (Year: 2017).*

(Continued)

*Primary Examiner* — Erica S Lee
(74) *Attorney, Agent, or Firm* — Kolitch Romano Dascenzo Gates LLC

(57) ABSTRACT

An assembly for anchoring in tissue may include an anchor part and a biasing part. The anchor part has a support made of a resilient material and at least two needles. The needles have a stem and a tip end configured to engage tissue. A portion of the stem is embedded in the support. The needles are allowed to be positioned according to a first configuration. A biasing part is configured to position the anchor part according to a second configuration differing from the first configuration in an orientation of the needles relative to one another. The biasing part includes holding means configured to hold the anchor part in the second configuration. The support is allowed to be deformed, thereby acting as a pivot when the needles change between the first configuration and the second configuration.

20 Claims, 10 Drawing Sheets

(56) References Cited

U.S. PATENT DOCUMENTS

| | | | |
|---|---|---|---|
| 5,609,623 A * | 3/1997 | Lindegren | A61N 1/05 |
| | | | 607/128 |
| 9,662,487 B2 | 5/2017 | Kveen et al. | |
| 10,426,952 B2 | 10/2019 | Kveen et al. | |
| 10,463,853 B2 * | 11/2019 | Drake | A61N 1/057 |
| 2006/0015164 A1 * | 1/2006 | Partridge | A61N 1/0573 |
| | | | 607/119 |
| 2007/0010715 A1 * | 1/2007 | Sixto | A61B 17/068 |
| | | | 600/217 |
| 2011/0238077 A1 * | 9/2011 | Wenger | A61N 1/37512 |
| | | | 606/129 |

FOREIGN PATENT DOCUMENTS

| | | |
|---|---|---|
| WO | 2010128167 A1 | 11/2010 |
| WO | 2017178851 A2 | 10/2017 |

OTHER PUBLICATIONS

International Search Report and Written Opinion of the International Searching Authority from the European Patent Office, in PCT/EP2019/084742 dated Dec. 11, 2019, which is an international application corresponding to this U.S. application.

* cited by examiner

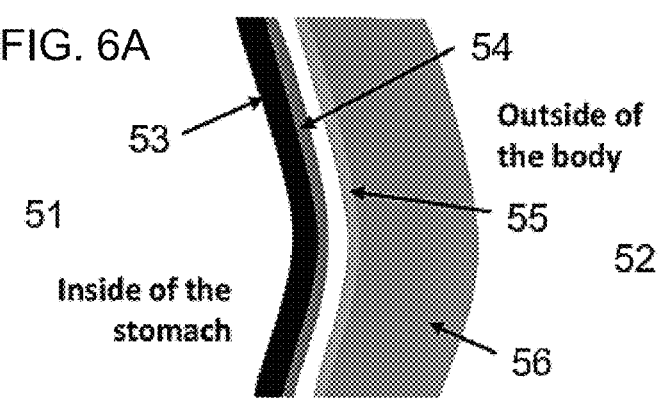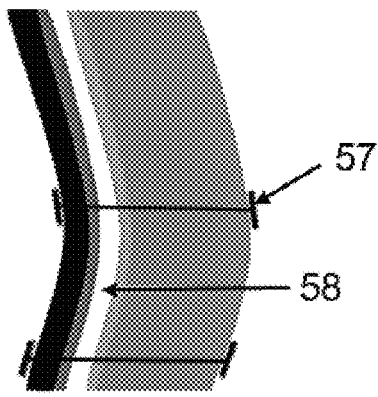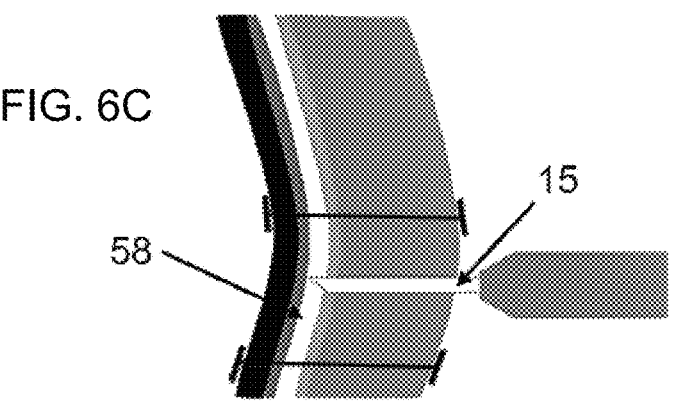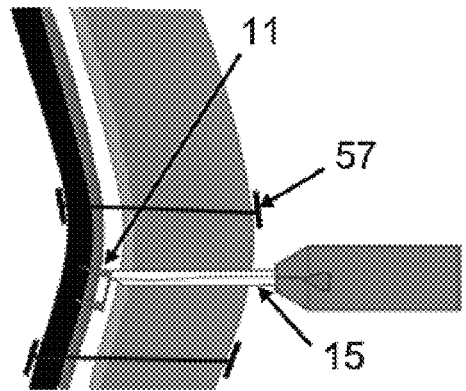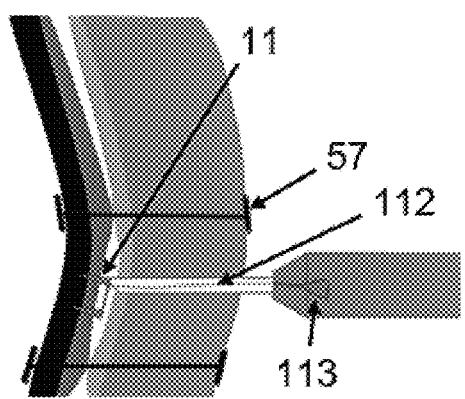

TISSUE ANCHORING ASSEMBLY

TECHNICAL FIELD

The present disclosure is related to an assembly comprising means that anchor in soft tissue. The assembly can be used in combination with a variety of medical devices, such as though not limited to electro-stimulation implants, which require an anchor in soft tissue and is particularly adapted in minimally invasive surgery.

INTRODUCTION

There exist a variety of electro-stimulation implants which need to be anchored in the body of a living being. One such device is a gastro-stimulation device used for delivering electric stimulating signals to tissues of the stomach for treating obesity. A device of the above kind is known from WO 2010/128167. Another kind of such devices are muscle stimulation devices, in particular for epicardial stimulation.

A known problem with such devices is providing a good anchoring of the electrodes of such devices in tissues of interest. These tissues are often soft, but tough, such as muscular tissue, and/or difficult to access, such as serous tissue.

It is known from U.S. Pat. No. 4,066,085 to provide a contact device for applying stimulating pulses to cardiac muscle tissue. The device comprises needle-like attaching members which have a central part that is embedded in a base member. The ends of the attaching members are sharpened and spring outwardly to make them suitable for digging into and fixedly engaging tissue. The attachment members and the base member are sufficiently resilient to allow them to be flexed or folded by a pair of forceps. When folded, the attachment members are oriented substantially parallel to one another allowing them to engage tissue by pressing them against the selected site. Forceps are then slowly released which unfolds the base member and flexes the attachment members to spring outwards thereby forming a locking engagement with tissue.

One disadvantage of the above device is that the use of the forceps requires considerable operating space, which is not at hand during minimally invasive surgery. In fact, the forceps must be pivoted to an open position at the implant site in order to lock the device to tissue. As a result, considerable lateral space is required. Another disadvantage is that the forceps must be used both for flexing the base member and for pushing the device into engagement with the tissue. This requires quite some manual skill and may be problematic when the device is to be implanted in tough tissues.

It is known from U.S. Pat. No. 3,976,082 to provide an intercardial stimulation electrode comprising a plastic sleeve which houses a cylindrical slide that is allowed to slide inside the sleeve. The rear ends of a number of bristles are embedded in the slide. The tip ends of the bristles project from bores provided in a front terminal wall of the sleeve. The slide is moved by means of a catheter which extends into the sleeve. The catheter can move the slide from a rearward position, in which the bristles are retracted in the sleeve, and a forward position, in which the bristles eject from the front bores. A restriction in the sleeve acts as an abutment maintaining the slide in the desired position.

One disadvantage of the above assembly is that the slide must remain within the sleeve, even after positioning at the target site. This not only increases the bulkiness of the assembly that is left at target site after operation, but also requires additional measures to make the sleeve fluid tight, which increase cost.

SUMMARY

It is an aim of aspects of the present disclosure to provide anchoring assemblies or devices which overcome the drawbacks of the prior art. It is an aim of aspects of the present disclosure to provide such anchoring assemblies which are easier to use and require less effort and skill for implanting. It is an aim of aspects of the present disclosure to reduce operating space required for implant and hence which are truly minimally invasive, in particular which allow single hole laparoscopic surgery. It is an aim of aspects of the present disclosure to provide anchoring assemblies which are more economical and/or easier to manufacture.

It is an aim of aspects of the present disclosure to provide assemblies or devices which allow for an improved anchoring in tissue, e.g. with less probability of release from tissue and/or stronger attachment.

According to a first aspect of the present disclosure, there is therefore provided an assembly for anchoring in tissue. Assemblies according to aspects of the present disclosure comprise an anchor part and a biasing part, which may or may not be removable from the anchoring part. The anchoring part comprises a support and at least two needles coupled to the support. The support has a distal face and a proximal face, opposite the distal face. The at least two needles each have a tip end, a head end opposite the tip end and a stem extending from the head end to the tip end. At least a portion of the stem of each of the at least two needles is embedded in the support. The tip end is configured to engage tissue and projects from the distal face. The at least two needles are configured to adopt a first configuration relative to one another. The biasing part is configured to position the anchor part, in particular the at least two needles, according to a second configuration, wherein the second configuration differs from the first configuration in an orientation of the at least two needles relative to one another.

According to an aspect, the biasing part comprises holding means (or a holding device) configured to engage the anchor part in a manner as to hold the anchor part in the second configuration. Advantageously, the holding means are locking means, configured to engage the anchor part in a manner as to lock the anchor part, in particular the needles, in the second configuration. As a result, the at least two needles are maintained in the second configuration due to the holding/locking means and there is advantageously no external force that must be applied, such as from an operator, to maintain the holding means in place.

The support is made of a resilient material, such as an elastic, elastomeric or flexible material. The support can be formed as a body having any suitable shape, such as cylindrical, prismatic or parallelepiped. The proximal face forms one end of the support body, and the distal face forms an opposite end. The anchor part can thus be obtained, e.g. by molding the support body about the at least two needles, e.g. when in the first configuration. By so doing, stem portions of the at least two needles become embedded in the resilient material of the support.

The needles are advantageously rigid. As the at least two needles are embedded in the support, the at least two needles can only change between the first configuration and the second configuration while the support deforms, due to the resiliency of the support. The support therefore acts as a pivot for the at least two needles during the configuration change. Therefore, in order to change needle orientation, the support is deformed—either directly by acting on the support, or indirectly by acting on the needles which must deform the support in order to change orientation. The head ends of the needles are advantageously spaced apart in at least one, possibly in both of the first orientation and the second orientation.

Either the first configuration, or the second configuration can correspond to a deployed configuration, wherein the at least two needles are diverging from one another towards the tip ends. The other configuration of the two can correspond to a non-deployed configuration, wherein the at least two needles are substantially parallel, or diverging from one another with a first angle of divergence being at least 20°, preferably at least 25°, at least 30°, or even at least 35° smaller than a second angle of divergence of the deployed configuration.

Advantageously, the support is configured to hold the needles in the first configuration, advantageously corresponding to an undeformed or uncompressed state of the support. Advantageously, the biasing part comprises engagement means for engaging the head ends, possibly in a releasable manner. The engagement means are advantageously shaped to force the at least two needles into the second configuration. The engagement means are advantageously formed as recesses configured to accept the head ends of corresponding needles. The head ends and the recesses may be suitably shaped for optimal engagement and/or force transmission.

The at least two needles may be solid or hollow. They are advantageously rigid and may be made of a biocompatible material, preferably metal, such as a titanium alloy or a biocompatible stainless steel. The needles may be configured to operate as electrodes, in which case they are advantageously electrically conducting. A distal part of the needles, adjacent the tip ends may be electrically conducting, whereas a proximal part of the needles, adjacent the head ends may be electrically isolated, e.g. comprising an isolating sheath.

In a second aspect, there is described a delivery system. The delivery system is advantageously used in combination with assemblies of the present disclosure. Advantageous delivery systems comprise a tubular member comprising a lumen opening into a recess at a distal end. The recess is configured to accommodate the support. The lumen can be configured to accommodate the biasing part and to deliver the biasing part along the lumen to the distal recess. Alternatively, the recess can act as the biasing part by having a size smaller than the support. The recess may comprise means for force transmitting engagement with the support, which may be an axial force (e.g., aligned along a proximal-distal direction), a torque, or a combination of both. The distal recess advantageously allows to convert from one needle configuration to the other one with minimal space requirements, e.g. only a pushing and/or twisting force is required for implanting the anchor part. This allows for using present assemblies in situations where there is little space for manipulation of medical instruments such as forceps.

According to a third aspect, there is described a method of implanting the assembly into tissue according to the first aspect hereinabove.

BRIEF DESCRIPTION OF THE DRAWINGS

Aspects of the present disclosure will now be described in more detail with reference to the appended drawings, wherein same reference numerals illustrate same features.

FIG. 1a represents the different parts of the tissue anchoring assembly; FIG. 1b represents the tissue anchoring assembly of FIG. 1a in a biased configuration, in which the needles are not deployed (non-deployed) and ready for penetrating into tissue; FIG. 1c represents the tissue anchoring assembly of FIG. 1a in a non-biased configuration, in which the needles are deployed and lock into tissue. FIG. 1d represents a front view of the tissue anchoring member in the configuration of FIG. 1b and FIG. 1e represents a front view of the tissue anchoring member in the configuration of FIG. 1c.

FIG. 2a represents the different parts of the tissue anchoring assembly in a non-biased configuration, in which the needles are not deployed and ready for penetrating into tissue; FIGS. 2b and 2c represent the tissue anchoring assembly of FIG. 2a in a biased configuration, in which the needles are deployed and lock into tissue. FIG. 2d represents a front view of the tissue anchoring member in the configuration of FIG. 2a; and FIG. 2e represents a front view of the tissue anchoring member in the configuration of FIG. 2b.

FIGS. 3a and 3b represent perspective views in a non-biased and a biased configuration respectively; FIG. 3c represents a perspective exploded view; FIGS. 3d and 3e represent top views of the biasing member and needle positions in the non-biased and biased configuration respectively.

FIG. 4a shows the anchor part with needles in a deployed configuration. FIG. 4b shows the anchor part with needles in a non-deployed configuration.

FIG. 5a represents the anchor part held in the biasing part (biased and non-deployed configuration). FIG. 5b represents the anchor part attached to the tissue (non-biased and deployed configuration).

FIGS. 6a-j represent schematically different steps in a procedure of implanting anchoring assemblies on the peritoneum of the stomach. Transverse schematic views of the tissues are represented.

DETAILED DESCRIPTION

Figure 1A:
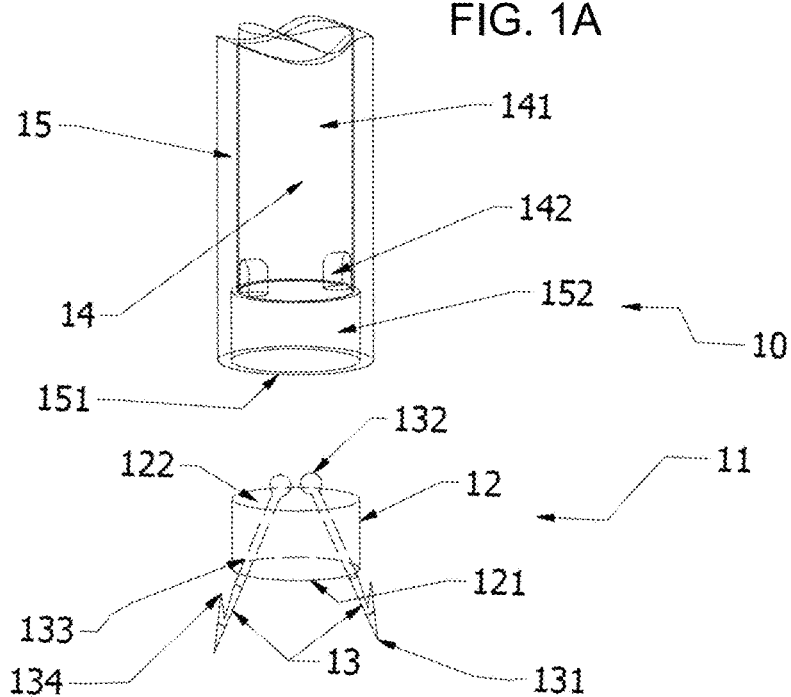
FIGS. 1a-e represent perspective views of a tissue anchoring assembly according to a first embodiment.

Referring to FIG. 1a, a first embodiment of a tissue anchoring assembly 10 is shown, which comprises an anchor part 11 configured to be anchored at a selected site of a human or animal body, a biasing member 14 which is releasable from the anchor part 11 and, optionally, a delivery system 15, e.g. a trocar or other surgery lumen or any natural opening in the body, allowing to deliver the anchor part 11 and the biasing member 14 to the selected site.

The selected site can be any internal or external site of the body, e.g. internal (soft) tissue, such as though not limited to muscle tissue, visceral tissue, serous tissue, mucosa, etc., or external tissue, such as the skin or exposed mucosa.

The anchor part 11 comprises a support 12 and a pair of needles 13 or any needle-like member allowing for penetrating the tissue at the selected site. There may be more than two needles 13, e.g. four. The support 12 is advantageously made of a resilient or suitably elastic material, e.g. polydimethylsiloxane (PDMS) compounds (PDMS silicones) or rubber, advantageously a biocompatible silicone. The support is advantageously made of a material having a 100% modulus (M100 or tensile stress at 100% elongation) between 140 kPa and 700 kPa. The support 12 is formed as a body and comprises a distal face 121 and a proximal face 122 arranged opposite the distal face 121. Each needle 13 comprises a needle tip 131 and a head 132 arranged at the opposite end of the needle 13 compared to the tip. The needle further comprises a stem 133 extending from the head 132 to the tip 131. To enhance the locking into tissue, the needle 13 advantageously comprises one or more barbs 134.

Each needle 13 is attached to the support 12. In particular, a portion of the stem 133 may be embedded in the support, from the proximal face 122 to the distal face 121. By so doing, the support may keep the needles 13 in place as desired. The needle tip 131 projects outwardly from the distal face 121, whereas the needle head 132 advantageously projects outwardly from the proximal face 122.

As seen in FIG. 1*a*, in a non-biased state, the anchor part 11 assumes a first configuration in which the needles 13 diverge from one another towards the tip 131. This first configuration corresponds to a locking configuration once the needles 13 have penetrated tissue, since the divergent orientation of the needles 13 will prevent disengaging from tissue. In this configuration, and referring to FIG. 1*e*, the needles are advantageously oriented at an angle α between 20° and 70° with respect to an axis 101 of the support 12. Axis 101 is aligned along the proximal-distal direction, and may be perpendicular to the distal face 121, the proximal face 122 or both. The angle α is advantageously between 30° and 65°, advantageously between 35° and 60°.

Figure 1B:
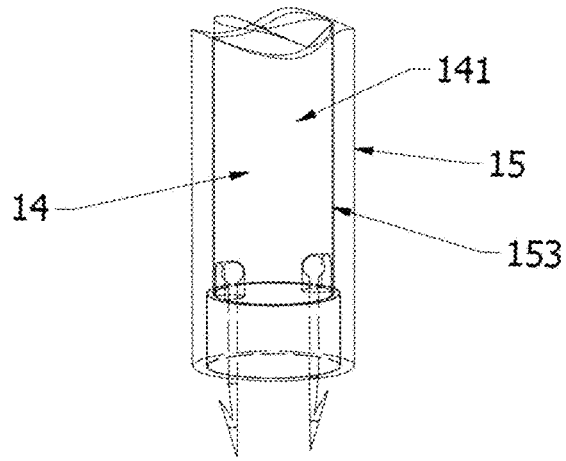
Figure 1C:
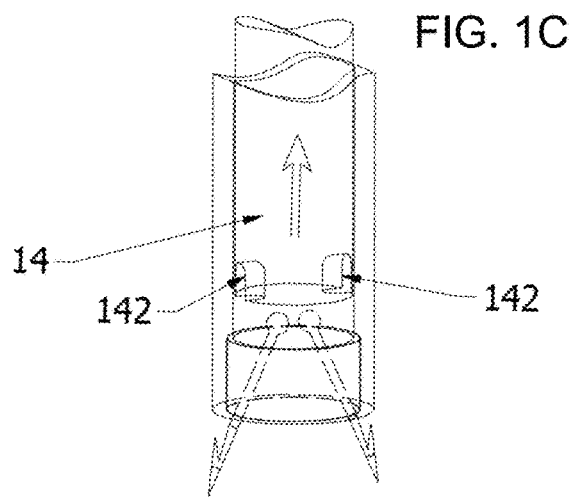
Figure 1D:
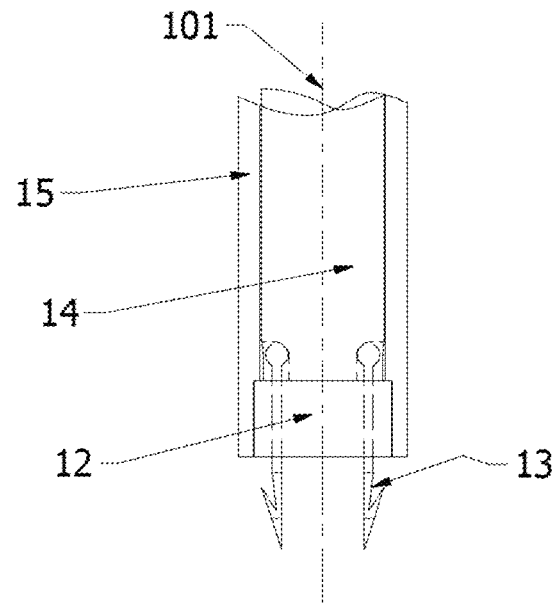

Referring to FIGS. 1*b* and 1*d*, in order to enable the anchor part 11 to penetrate tissue, biasing member 14 comprises a body 141 and recesses 142 arranged at a distal end of the body 141. Each recess 142 is configured to accept the head 132 of a needle 13. The recesses 142 are spaced apart at a distance which maintains the needle heads 132 spaced apart from one another at greater distance as compared to the non-biased configuration shown in FIG. 1*a*. Since the support 12 is resilient, it advantageously acts as a pivot so that the needles 13 change orientation relative to one another. The biasing member 14 therefore allows for maintaining the anchor part 11 in a second, biased, configuration. In this configuration, the needles 13 are advantageously oriented substantially parallel to one another, e.g. within a margin of +/−15°, advantageously a margin of +/−10°. Alternatively, the needles 13 may be oblique relative to axis 101 in the biased configuration, with an angle between needle 13 and axis 101 substantially smaller than α of the non-biased configuration, e.g. smaller by at least 25°, advantageously smaller by at least 30°. The orientation of the needles 13 relative to the support 12 is advantageously such that substantially simultaneous penetration of the needle tips 131 into tissue is made possible.

The biasing member 14 can be releasable from the anchor part 11 prior to operation or surgery, e.g. prior to insertion in the body. There are various ways in which this is made possible. By way of example, the needle tips 131 are moved towards one another. Since the support 12 is acting as a pivot, the needle heads 132 will move apart and allow inserting the heads 132 in the recesses 142 of the biasing member 14.

Figure 1E:
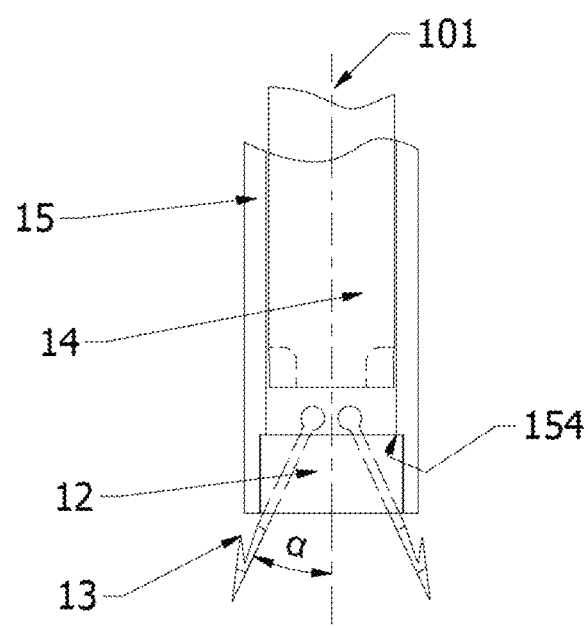

A delivery system 15 is advantageously used for delivering the assembly of anchor part 11 and biasing member 14 to the selected site, which can be inside the body, or external. Delivery system 15 advantageously comprises a lumen 153 having a distal open end 151. A recess 152 is provided at the open end 151 for accommodating the anchor part 11. Lumen 153 advantageously allows for slidably accommodating the biasing member 14. Referring to FIGS. 1*d* and 1*e*, an appropriate abutment 154 for the anchor part 11 is provided in recess 152. The abutment 154 can be formed by a shoulder between recess 152 and lumen 153, e.g. by making recess 152 of larger diameter compared to the diameter of lumen 153. The support 12 is configured to abut against abutment 154 when inserted from the open end 151. In this regard, it will be convenient to note that the biasing member 14 may have a diameter which is smaller than a diameter of the support 12, so as to fit in lumen 153.

A procedure for locking the anchor part in tissue may start with coupling the biasing member 14 to the anchor part 11. The needle heads 132 are accommodated in corresponding recesses 142, which makes the needles 13 assume a biased, or—in the instant case—non-deployed configuration. Next, the anchor part 11 with biasing member 14 coupled thereto is delivered to the site of interest, e.g. by means of delivery system 15, with anchor part 11 accommodated in recess 152 and biasing member in lumen 153. In the biased configuration, the needles 13 assume an orientation fit for engaging and penetrating tissue. The anchor part 11 is now pushed towards the tissue, by pushing delivery system 15 which exerts a pushing force on the support 12 through abutment 154, or by pushing biasing member 14, or both. By so doing, needles 13 are made to engage and penetrate tissue when still in the biased configuration as shown in FIG. 1*b*. Next, the delivery system 15 may be maintained in place, while the biasing member 14 is pulled in proximal direction as illustrated by the arrow in FIG. 1*c*. The abutment 154 will keep the anchor part 11 in place. As the recesses 142 are withdrawn from the needle heads 132, the biasing force on the needles 13 is removed, and the resiliency of the support 12 brings the needles 13 back to their normal, non-biased configuration as shown in FIG. 1*c*. In this configuration, the needles diverge from one another as being deployed and lock into the tissue. The delivery system 15 and biasing member 14 can now be removed.

Figure 2A:
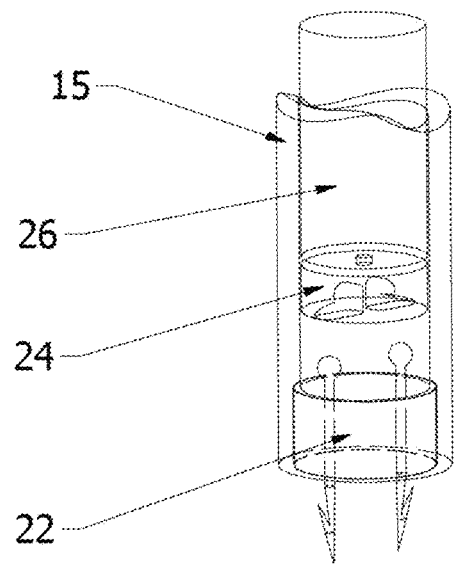
FIGS. 2a-e represent perspective views of a tissue anchoring assembly according to a second embodiment.

Referring to FIGS. 2*a*-*e*, in a second embodiment of a tissue anchoring assembly 20 according to aspects as described herein, in the non-biased configuration as shown in FIG. 2*a*, the needles 13 are attached to the support 22 in an orientation substantially parallel to one another, allowing them to penetrate into tissue. A same delivery system 15 as for the first embodiment can be used for delivering the anchor part 21 to the implant site and for penetrating tissue by pushing delivery system 15 on the tissue. The abutment 154 will then push on the support 22 and therefore the needles 13 will be pushed into the tissue. In this non-biased configuration, corresponding to a non-deployed configuration, the needles 13 can be oriented identically to the orientation of the needles in the biased configuration of the first embodiment (FIG. 1*b*).

Figure 2B:
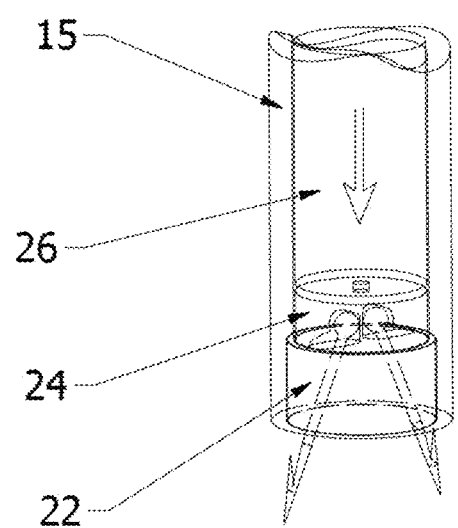
Figure 2C:
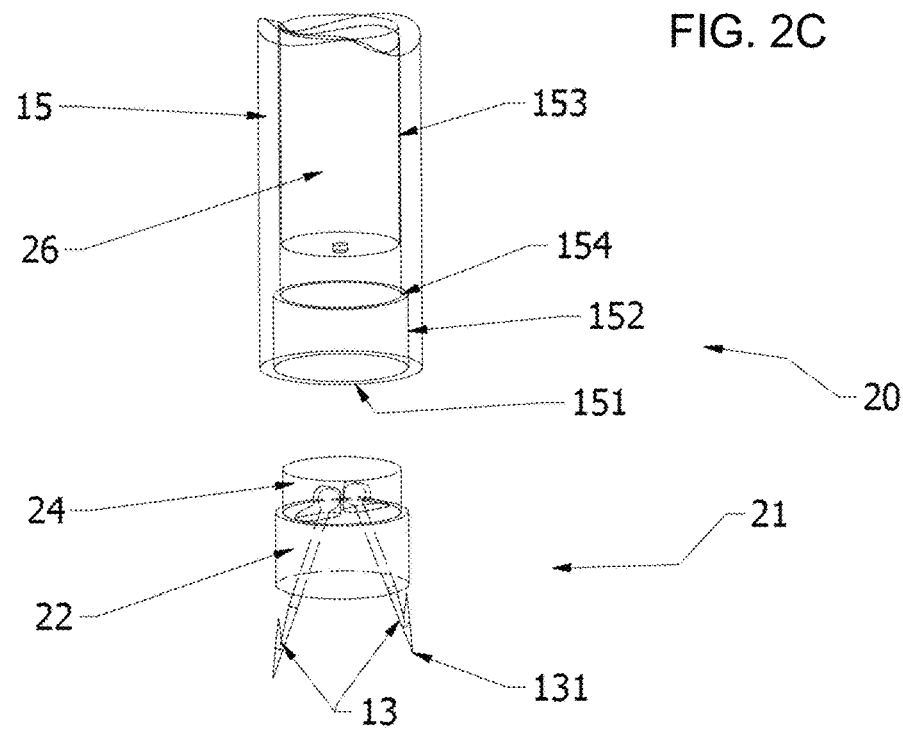
Figure 2D:
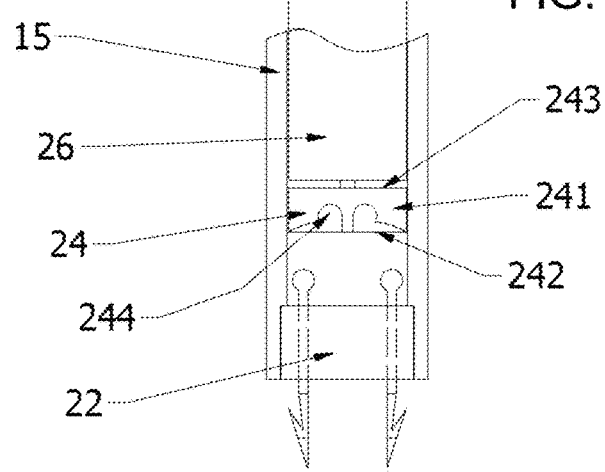
Figure 2E:
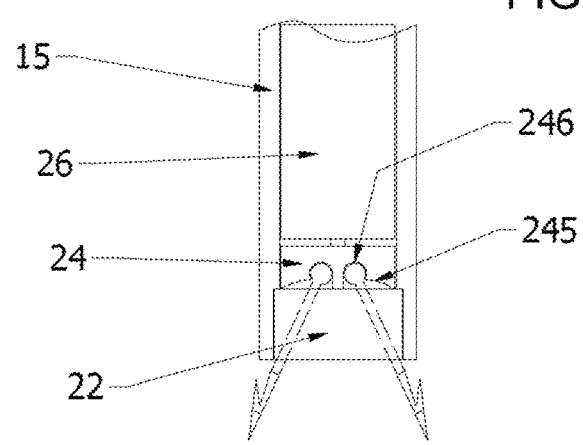

With the needles 13 having penetrated into tissue, and referring to FIG. 2*b*, the biasing member 24 is now pushed down the lumen 153 to abut against the anchor part 21. The biasing member 24 can be pushed towards the anchor part 21 in the direction of the arrow illustrated in FIG. 2*b* with the aid of an auxiliary member 26 which may, or may not be (releasable) attached to the biasing member 24. The auxiliary member 26 may be any suitable push member, such as a push rod.

Biasing member 24 is advantageously formed of, or comprises a body 241 having a distal face 242 and a proximal face 243 opposite the distal face 242. The biasing member 24 is disposed so as to engage or otherwise interface the anchor part 21 with its distal face 242 and to engage or interface the auxiliary member with its proximal face 243. Recesses 244 are provided on the distal face 242 of the biasing member 24, configured to accept corresponding needle heads 132. The recesses 244 are suitably shaped to bias the needle heads 132 towards one another and lock the heads in place. In this biased configuration (FIG. 2b), the needle heads 132 are spaced closer to one another as compared to the non-biased configuration of FIG. 2a. As the support 22 acts as a resilient body and therefore as a pivot, the needles 13 are brought in an orientation in which they diverge from one another in a direction towards the needle tips 131. The orientation in the biased configuration can be identical to the non-biased orientation of the first embodiment (FIG. 1e).

The recesses 244 are advantageously shaped such that they allow moving the needle heads 132 towards one another when pushing the biasing member 24 on the needle heads 132. In addition, the shape of the recesses 244 and/or of the needle heads 132 is advantageously formed such that the needle heads 132 can be locked in the recesses 244. This allows for locking the biasing member 24 on the anchor part 21, and hence for maintaining the needles 13 in the biased configuration which in turn allows for locking the needles in the tissue. In this regard, the recesses 244 can have a first part 245 for biasing/moving the needles from the non-biased configuration to the biased configuration, and a second part 246 which locks the needles in the biased configuration. The first part 245 is shaped to enable moving the needle heads 132 by applying a pushing force on the heads, in particular a force acting parallel to axis 101. The second part can be shaped to lock the needle heads in place by any suitable mechanism, such as though not limited to a snap-fit mechanism. The biasing member 24 may be removable from the needles and/or the support.

Once the biasing member 24 having been pushed to lock with the needle heads 132 by auxiliary member 26, auxiliary member 26 is advantageously removed or detached from engagement with the biasing member. Auxiliary member 26 may be attached to the biasing member 24, e.g. with any suitable releasable or frangible coupling. The auxiliary member 26 can be removed from the implant site along with delivery system 15, leaving biasing member 24 (permanently) attached to anchor part 21.

Figure 3A:
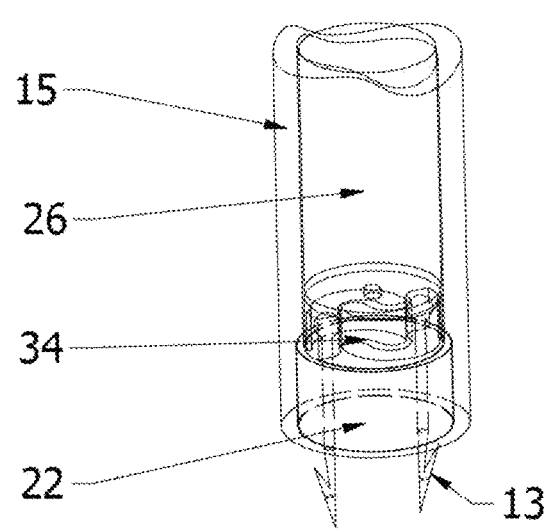
FIGS. 3a-e represent views of a tissue anchoring assembly according to a third embodiment.
Figure 3B:
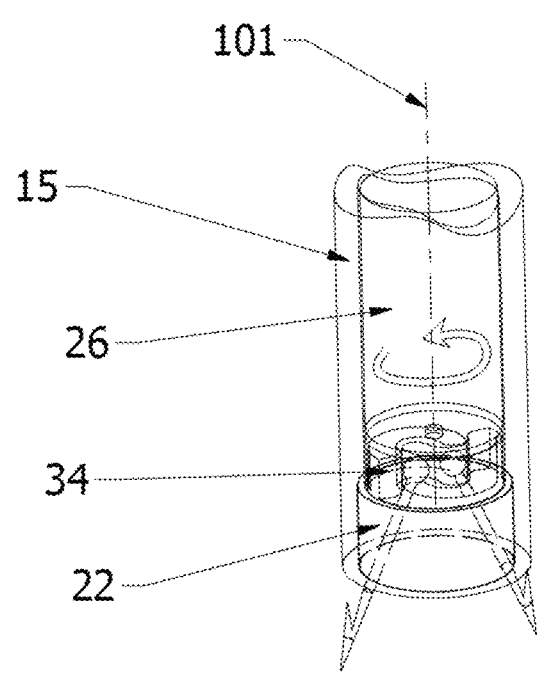
Figure 3C:
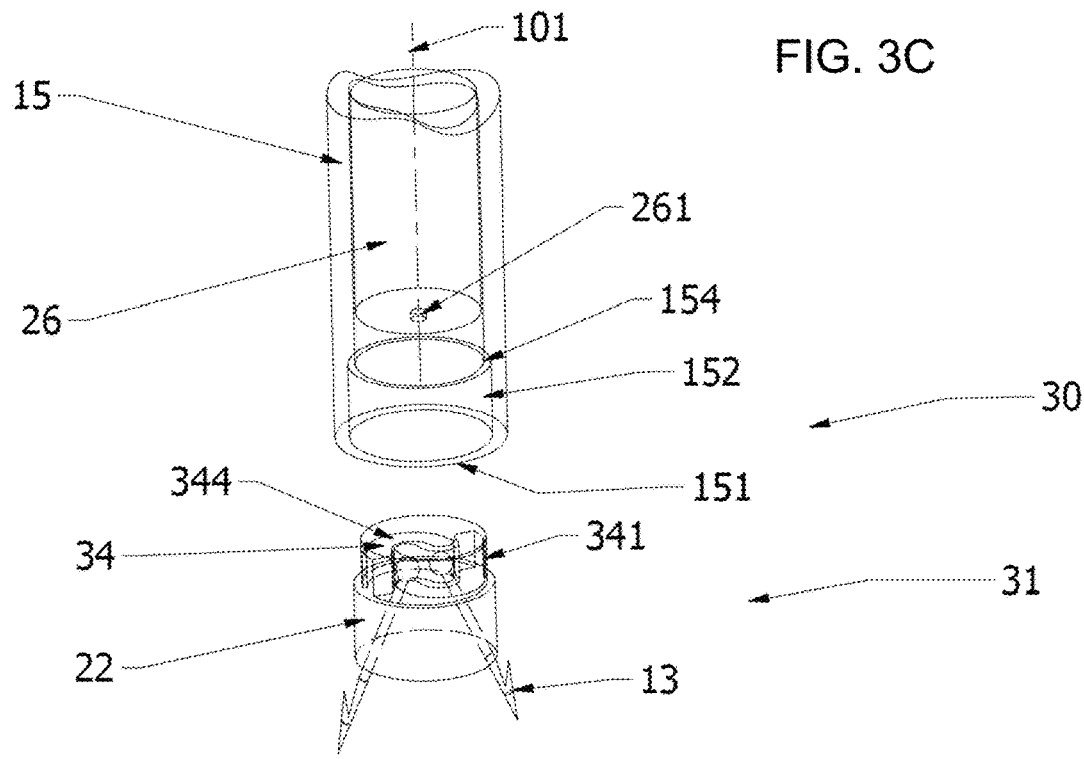
Figure 3D:
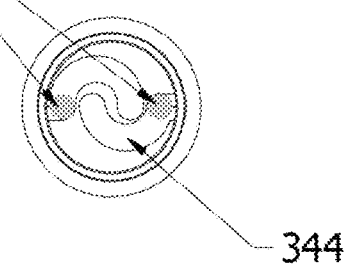
Figure 3E:
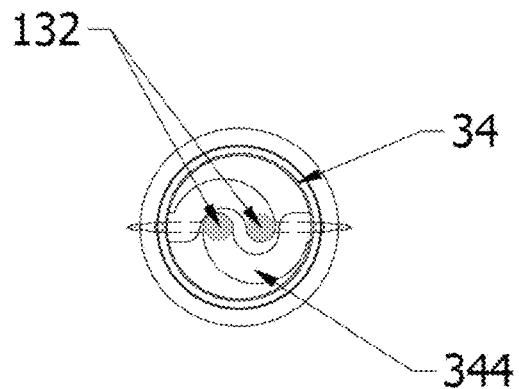

With reference to FIGS. 3a-e, a third embodiment of a tissue anchoring assembly 30 differs from assembly 20 in that the biasing member 34 is configured to bias the needles 13 from a non-biased configuration as shown in FIGS. 3a and 3d to a biased configuration as shown in FIGS. 3b and 3e by twisting motion, rather than pushing as in assembly 20. Similar to the second embodiment, in this third embodiment, the non-biased configuration corresponds to the configuration in which the needles are positioned in an orientation suitable for penetrating the tissue, like the non-biased configuration of the second embodiment. The needles are maintained in the non-biased configuration by the support 22, which may be substantially identical to the support of the second embodiment, and e.g. may embed part of the needle stems 133. By way of example, the needles 13 may be substantially parallel to one another, or slightly diverging.

The support 22 can be delivered to the implant site with a delivery system 15, which may be identical to the ones described in relation to the first and second embodiment hereinabove. The support 22 can be inserted in a distal opening 151 of delivery system 15 and accommodated in recess 152. An abutment, such as shoulder 154 can be provided to enable exerting a pushing force on the support 22 so that needles 13 penetrate the tissue. Delivery system 15 can further accommodate a biasing member 34 and auxiliary member 26, e.g. in lumen 153.

Biasing member 34 is advantageously formed of, or comprises a body 341 comprising a number of recesses 344 corresponding to the number of needles 13. Recesses 344 are configured to accept corresponding needle heads 132 in the non-biased configuration (FIG. 3a, d). Additionally, recesses 344 are suitably shaped to allow to move the needle heads 132 towards one another and therefore to bring them from the non-biased configuration to the biased configuration and advantageously to lock the needle heads 132 in place. The biased configuration (FIG. 3b, e) is advantageously identical to the biased configuration of the second embodiment, with the needle heads 132 spaced closer to one another as compared to the non-biased configuration of FIG. 3d. As the support 22 acts as a resilient body and therefore as a pivot, the needles 13 are brought in an orientation in which they diverge from one another in a direction towards the needle tips 131, just as with the second embodiment above allowing to enter into locking engagement with the tissue.

Unlike the second embodiment, where transition from the non-biased orientation to the biased orientation of the needles is effected through pushing the biasing member 24 on the support 22, in the present embodiment the transition is effected through a twisting motion of the biasing member 34 relative to the support 22. In this regard, referring to FIGS. 3d and 3e, the recesses 344 are spiral-like shaped forming guides for the needle heads 132 to move them from the non-biased configuration (FIG. 3d) to the biased configuration (FIG. 3e) by twisting the biasing member 34 about axis 101 (see e.g. the arrow in FIG. 3b).

The recesses 344 are additionally advantageously shaped to lock the needle heads 132 in position when in the biased configuration, e.g. by providing a non-return trap in the guiding path of recess 344 preventing the needle head to move back.

The implant procedure is substantially similar to the second embodiment, except for locking the biasing member 34. The procedure may start with delivering the anchor part 31 to the site of interest, e.g. by means of delivery system 15, with support 22 accommodated in recess 152. The anchor part 31 is in the non-biased configuration and the needles 13 therefore non-deployed and fit to engage and penetrate tissue. In this configuration, the biasing member 34 may or may not be attached to the anchor part 31. If attached, the biasing member 34 is positioned as illustrated in FIG. 3d, with needle heads 132 positioned at one end of the recesses 344 corresponding to the non-biased configuration.

The anchor part 31 is now pushed towards the tissue, by pushing delivery system 15 which exerts a pushing force on the support 22 through abutment 154. Additionally, or in the alternative, biasing member 34 can be pushed towards the anchor part 31, e.g. by means of an auxiliary member 26 which may act as push rod. By so doing, needles 13 are made to engage and penetrate tissue when still in the non-biased configuration as shown in FIG. 3a. Next, the delivery system 15 may be maintained in place, while the biasing member 34 is twisted relative to the support 22 as illustrated by the arrow in FIG. 3b. To this end, the delivery system 15 may comprise torque-transmitting means to prevent rotation of the support 22 in twisting direction (direction of the arrow in FIG. 3b), such as one or more hooks or suitable projections fitting in corresponding recesses of the support to prevent rotation (not shown). By twisting the biasing member 34 relative to the support 22, the needles 13 are brought from the non-biased configuration to the biased configuration. In the latter configuration, the needle heads 132 are moved or guided along the corresponding recesses 344 from one end to an opposite end, as shown in FIG. 3e. In the biased configuration, the needles are deployed and enter into a locking engagement in the tissue resulting in implant of the anchor part 31. The delivery system 15 and optionally the auxiliary member 26 can now be removed.

Biasing member 34 and auxiliary member 26 may or may not be attached to each other, e.g. through a removable or frangible coupling. Auxiliary member 26 is configured to drive the biasing member 34 to exert a twisting motion relative to support 22. Any suitable torque-transmitting coupling 261 between auxiliary member 26 and biasing member 34 can be used for this purpose.

It will be convenient to note that in the third embodiment, the abutment 154 is not required, since during tissue penetration, a pushing force can be exerted on the support 22 through auxiliary member 26 and/or biasing member 34.

The needles 13 may be made of any convenient material, advantageously metal, such as titanium or a biocompatible stainless steel. They may be hollow or solid.

Figure 4A:
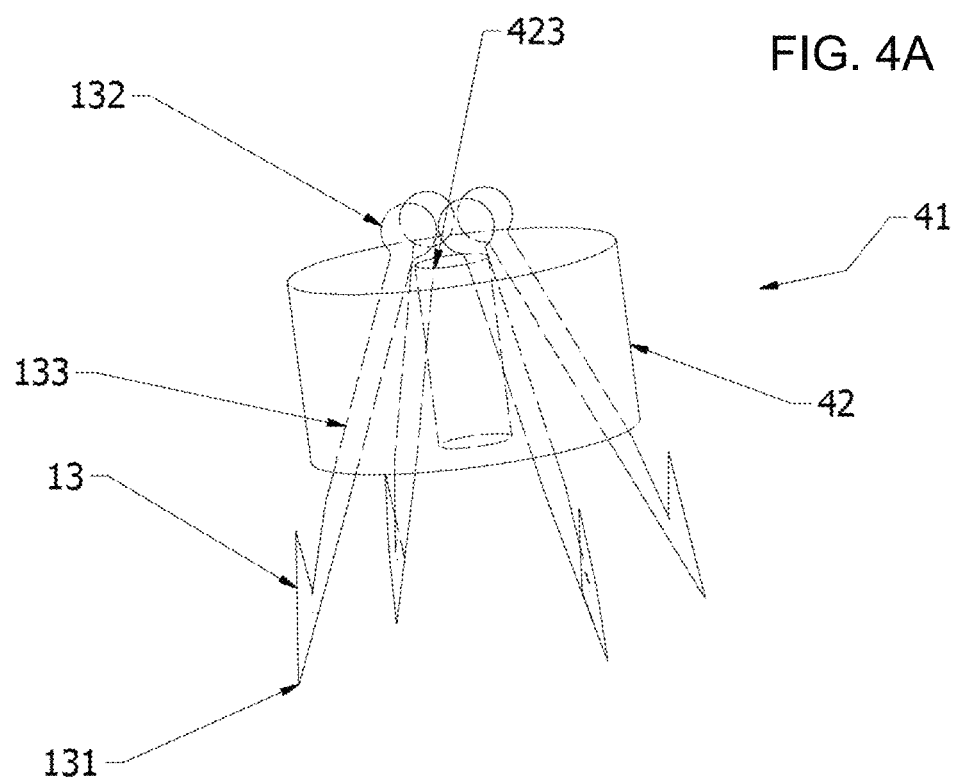
FIGS. 4a-b represent perspective views of an anchor part comprising four deployable tissue engagement needles in accordance with aspects of the present disclosure.
Figure 4B:
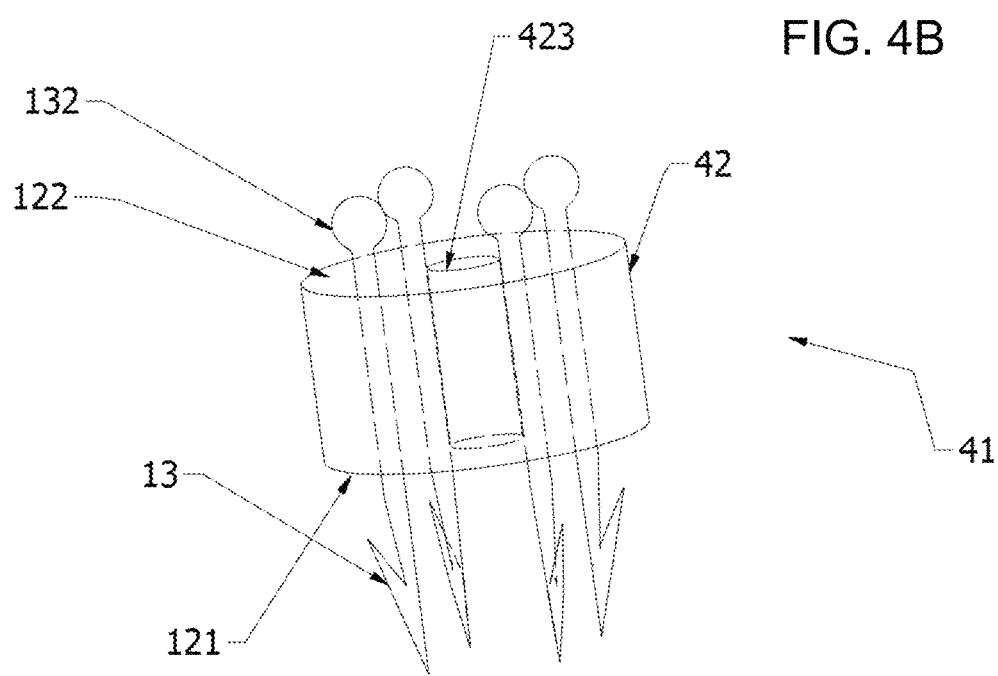

It will also be convenient to note that instead of having the needles diverge towards their tips in the deployed configuration, i.e. when in a locking engagement in tissue, the needles may also be made to converge towards their tips, which may provide an equivalent locking engagement, with the angle α between −20° and −70° with respect to axis 101. Referring to FIGS. 4a-b, an anchor part 41 is shown comprising more than two needles, in particular four needles. Anchor part 41 can be used in the same way as the anchor parts 11, 21 and 31 of the first to third embodiments. That is, the biasing members 14, 24 and 34, appropriately modified to accommodate four instead of two needles, can all be used in conjunction with the anchor part 41 in order to bring the needles from a non-biased configuration to a biased configuration. The non-biased configuration can depend on the biasing member, and may correspond either to FIG. 4a, or to FIG. 4b. Anchor part 41 comprises a support 42 which embeds a portion of the stem 133 of each needle 13.

The support may comprise a through-hole, such as through-hole 423 in FIGS. 4a-b, extending between the distal face 121 and the proximal face 122. Through-hole 423 is advantageously positioned such that the needles 13 surround the through-hole. The through-hole may accept an electrode (not shown), such as for electro-stimulation. As the needles 13 lock the anchor part 41 in tissue, the electrode is maintained in contact with the tissue of interest to deliver electric stimulating signals. Alternatively, the through-hole may provide a direct access to the tissue from the proximal side, e.g. in order to deliver a drug thereto, or to withdraw a bodily fluid through the through-hole via a hollow needle inserted in the through-hole.

Alternatively, one or more of the needles 13 can be configured to act as electrodes. These needles can be electrically coupled to an electric stimulation circuit, which may be provided fixed to the anchor part, or remote therefrom and e.g. connected through an electric wire. The electric stimulation circuit may be embedded within the support of the anchor part, or within the biasing member, or (fixedly) attached thereto.

Figure 5A:
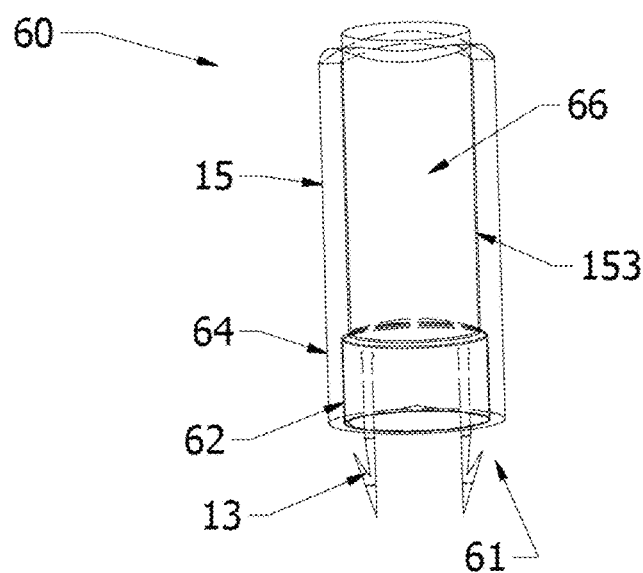
FIGS. 5a-b represent views of a tissue anchoring assembly according to yet another embodiment of the present disclosure.
Figure 5B:
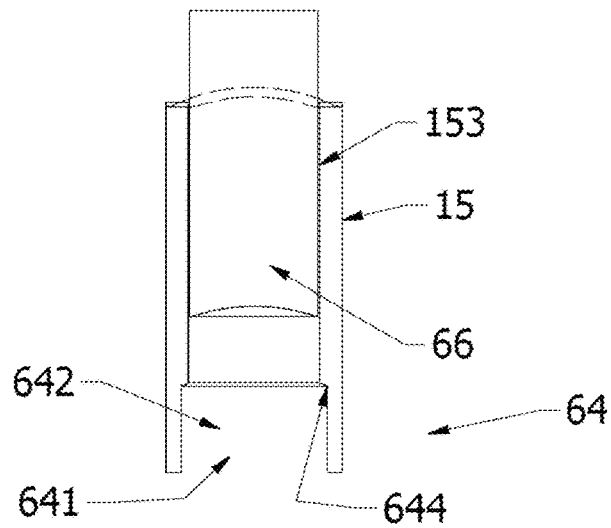
Figure 5B:
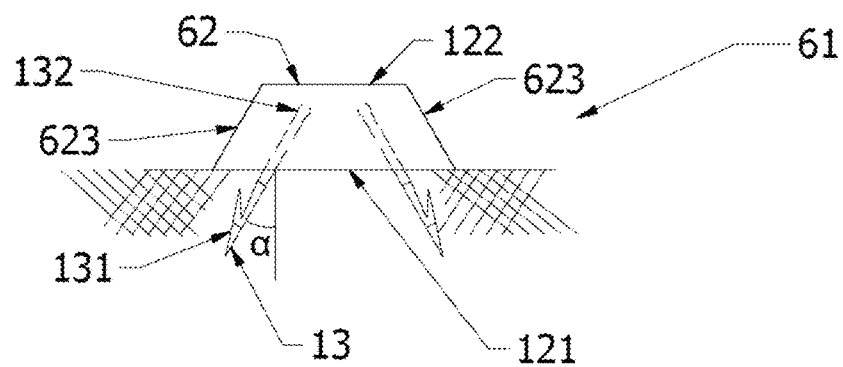

Referring to FIGS. 5a-b, tissue anchoring assembly 60 comprises an anchor part 61 and a biasing part 64. The anchor part 61 comprises a set of needles 13 each having a needle tip 131 and needle head 132, and a support 62. The support 62 is made of a resilient or flexible material, such as silicone or rubber, allowing it to be deformed. Unlike the previous examples, the needles 13 advantageously do not extend beyond the proximal face 122 of support 62. That is, the head ends 132 are embedded in the support. As shown in FIG. 5b, in a deployed configuration, the support 62 has a substantially planar distal face 121. The needles 13 advantageously project from the distal face 121 under an angle α with respect to a normal to the distal face 121, with values of α as indicated above. A sidewall 623 of the support 62 is advantageously inclined such that the distal face 121 has generally a larger area than the proximal face 122. Such inclination may aid in introducing the anchor part in the biasing part 64.

The biasing part 64 is advantageously integrated at an end of the delivery member 15. Biasing part 64 comprises a recess 642 having an access opening 641 at the distal end. The recess 642 advantageously has a cross sectional size (e.g., diameter or spacing between opposite side walls) that is smaller than a corresponding cross sectional size or diameter of the support 62. The support 62 will therefore need to be compressed in order to be accommodated in recess 642. By so doing, the needles will change orientation to a biased and non-deployed configuration, in which the needles may be substantially parallel in order to facilitate tissue penetration. Recess 642 is advantageously shaped to allow for force transmitting engagement with the support 62 when accommodated in the recess 64. To this end, a shoulder or flange 644 may be provided. While the anchor part 61 is accommodated in the biasing part 64, it can be made to penetrate the tissue by pushing the delivery member 15 in a distal direction. By so doing, the needles will penetrate into the tissue.

Delivery member 15 is advantageously hollow with lumen 153 communicating with recess 64. Lumen 153 slidingly accepts an auxiliary member 66 such as a push rod. Auxiliary member 66 can assist to maintain the anchor part 61 against the tissue while removing the anchor part 61 from the recess 64. Therefore, following tissue penetration, the delivery member 15 is withdrawn in proximal direction, while the auxiliary member 66 remains pressed against the anchor part 61. The anchor part 61 is removed from the recess 642 and automatically deploys in the unbiased state.

It will be convenient to note that providing appropriate anchoring for electro-stimulation devices is not the only possible application of anchoring assemblies as described herein. Another suitable application is for the delivery of solid or liquid drugs to a site of interest. Anchoring assemblies may be configured to deliver a treatment solution to the site of interest over a prolonged period. By way of example, one or more of the needles 13 may be made hollow and be connected to a reservoir configured to contain a treatment solution. In addition, or alternatively, the through-hole 423 may accommodate a catheter to deliver or drain solid, semi-solid or liquid material.

Referring to FIGS. 6a-j, in one example application, anchoring assemblies according to aspects of the present disclosure are attached to the peritoneum of the stomach. A similar procedure can be applied to all serous membranes. One property of the peritonea (and all serous membranes) that is exploited to an advantage in the present procedure is that they stick together when a sufficient pressure is applied during a certain time. Since all the inside of the abdominal cavity is covered by a serosa, and so is the outer surface of the stomach, it is possible to create a secured pocket located on the external stomach wall.

FIG. 6a, represents the different layers between the gastric cavity 51 and the outside of the body 52. From left to right: the gastric wall 53, the visceral peritoneum 54, which adheres to the gastric wall 53, the parietal peritoneum 55 and, adhering thereto, the abdominal wall 56 (formed successively of muscle, fat and skin tissue).

In a first step, FIG. 6b, a plurality of tags 57 (e.g. four, of which two are drawn) are implanted to engage the tissues between the gastric cavity 51 and the abdominal wall (i.e. tissues 53 to 56). Four tags 57 e.g. are positioned to form a square pocket 58 located between the visceral peritoneum 54 and the parietal peritoneum 55. The spacing between the tags 57 may e.g. be maximum about 2 cm. Tags 57 are not tightened/secured yet.

In a second step, FIG. 6c, a delivery system 15, e.g. formed as a hollow needle, with an outer diameter of 20 Fr (French gauge) maximum, which equals 6.6 mm, is inserted until it reaches the pocket 58.

In a third step, referring to FIG. 6d, the anchor part, e.g. 11 (but may be any anchor part as described herein) is delivered to the pocket 58 by means of the delivery system 15 and is anchored in the visceral peritoneum 54 and/or the gastric wall 53. Anchor part 11 may be delivered by accommodating it in a distal recess 152 of the delivery system (see e.g. FIG. 1a) prior to insertion of delivery system 15, or the anchor part 11 may be inserted once the delivery system 15 has reached pocket 58, e.g. through a lumen 153 of the delivery system 15. The anchor part is subsequently anchored in tissue by engaging and penetrating the tissues 53 and/or 54 with needles 13 and locking the tissue engagement by deploying the needles 13 by means of a biasing member as described hereinabove.

Needles 13 may act as electrodes in which case they are connected with an electric wire 112 to an electric connector 113 delivered through the delivery system 15. In a next, optional step, FIG. 6e, after the needles 13 have been correctly stuck into the stomach, the tags 57 may be tightened to fasten the structure. As a result, the pocket 58 is isolated from the outside, which enables an extra security because any infection occurring inside this pocket cannot propagate in the whole peritoneal cavity.

Figure 6F:
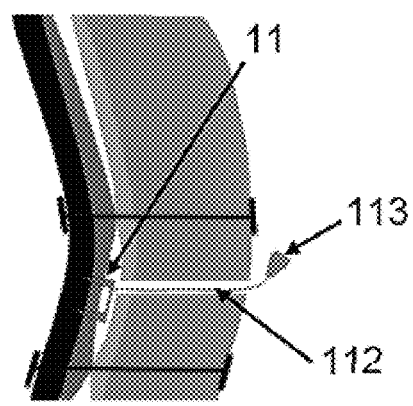
Figure 6G:
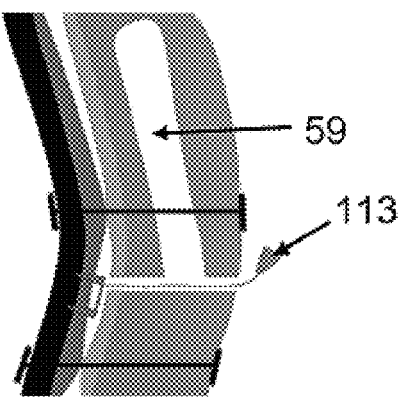
Figure 6H:
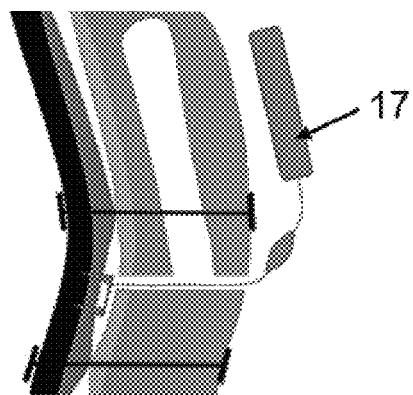
Figure 6I:
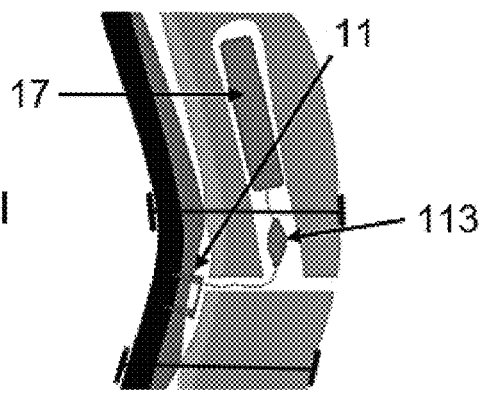
Figure 6J:
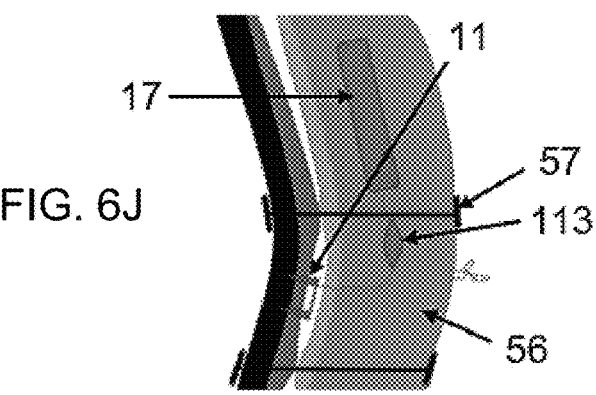

In a next step, FIG. 6f, the delivery system 15 is removed, leaving the electric wire 112 ending by connector 113. Referring to FIG. 6g, a subcutaneous pocket 59 is prepared for the implant, which can be a pacer, a generator, or any other suitable electrical device. Referring to FIG. 6h, a device 17 comprising an electronic circuit configured to provide signals for electro-stimulation is electrically connected to the needles 13 (acting as electrodes), e.g. through connector 113. The device 17 is put inside the subcutaneous pocket 59, FIG. 6i. Finally, FIG. 6j, the incision that was made to implant device 17 and/or to insert delivery system 15 is sutured. The electrical signals can be neural or muscular signals.

Advantages of the above procedure are that the incision reaching to the stomach (gastric wall 53) is reduced to a single hole which can be made very small, e.g. 6.6 mm diameter, while the larger subcutaneous pocket 59 receiving the device 17 is made in the abdominal wall 56 and therefore is more superficial. Additionally, due to the easier implanting procedure, no good view of the operation site is required and hence, insufflation is not necessary any more. The above procedure is therefore less invasive and involves less risk and faster recovery for the patient.

First experiments have been performed to test the long-term tissue anchoring of devices according to the present disclosure on the gastric wall of dogs. A device, with an angle α of 40°, with a margin of 10°, has been implanted in each of 6 dogs. CT-scan (computerized tomography) images have been obtained at regular intervals to check the position of the device and also to check that the mucosa was not transpierced. In a first dog, CT images were taken 4.5 months and 14.5 months after implant. The device was found to be at the same position without transpiercing of the gastric wall. In two other dogs, CT images were taken 1.5 months and 11 months post-implantation. The device was found to be well-positioned without transpiercing of the gastric wall. In a fourth, fifth and sixth dog, CT images were taken 5 days and 10 months post-implant. A same result as for the three first dogs could be deduced for the latter three dogs.

Second experiments have been performed to prove the feasibility of the implantation procedure on the gastric wall as described in relation to FIGS. 6a-j. A device, with an angle α of 45°, with a margin of 10°, has been implanted in each of 3 male pigs. The experiments concluded that the fixation of such anchoring system is feasible and meets the needs of lower implantation time and invasiveness.

The invention claimed is:

1. An assembly for anchoring in tissue, the assembly comprising:
    an anchor part, the anchor part comprising:
        a support having a distal face and a proximal face opposite the distal face,
        at least two needles, each having a tip end configured to engage tissue, a head end opposite the tip end, and a stem extending from the head end to the tip end, wherein the stem of each of the at least two needles is at least partially embedded in the support, such that the tip ends project from the distal face and the head ends project from the proximal face,
        wherein the at least two needles are positionable in a first configuration; and
    a biasing part configured to position the anchor part according to a second configuration differing from the first configuration in an orientation of the at least two needles relative to one another, wherein the biasing part is releasable from the anchor part;
    wherein the biasing part comprises a holding device configured to hold the anchor part in the second configuration, wherein the holding device comprises at least two recesses configured to accommodate corresponding head ends; and
    wherein the support comprises a resilient material, such that the support is deformable and acts as a pivot when the at least two needles change between the first configuration and the second configuration.

2. The assembly of claim 1, wherein in a deployed configuration being one of the first configuration and the second configuration, the at least two needles diverge from one another towards the tip ends.

3. The assembly of claim 1, wherein in a deployed configuration being one of the first configuration and the second configuration, the at least two needles diverge from one another towards the head ends.

4. The assembly of claim 1, wherein the support is configured to hold the at least two needles according to the first configuration.

5. The assembly of claim 1, wherein the holding device is configured to enter into locking engagement with the at least two needles.

6. The assembly of claim 5, wherein the head ends project from the proximal face, and wherein the holding device is configured to engage with the head ends.

7. The assembly of claim 6, wherein the holding device is configured to engage and lock the head ends by approaching the head ends in a direction parallel to a proximal-to-distal axis.

8. The assembly of claim 6, wherein the holding device and the head ends are configured to form a co-operating guide and slide, the guide being configured to engage the slide both in the first configuration and in the second configuration, wherein the guide is configured to allow a change between the first configuration and the second configuration to be effected through a twisting motion of the biasing part relative to the support.

9. The assembly of claim 1, wherein the support comprises a through hole extending between the proximal face and the distal face, wherein the at least two needles are arranged at a periphery of the through hole.

10. The assembly of claim 1, wherein the resilient material has a tensile stress at 100% elongation from 140 kPa to 700 kPa.

11. The assembly of claim 1, wherein the at least two needles are rigid.

12. The assembly of claim 1, wherein the assembly is implantable.

13. A device, comprising the assembly of claim 1 and an electronic circuit electrically coupled to the at least two needles, the electronic circuit being configured to deliver electrical signals to the at least two needles, or to record electrical signals captured by the at least two needles.

14. The device of claim 13, wherein the at least two needles are each made of an electrically conductive material at the tip end, and wherein the respective head ends are electrically isolated from the tip end.

15. The assembly of claim 1, wherein the at least two needles diverge from one another in a non-deployed configuration with at most a first angle of divergence, and the at least two needles diverge from one another in a deployed configuration with a second angle of divergence at least 20° greater than the first angle of divergence; wherein the non-deployed configuration is one of the first configuration or the second configuration, and the deployed configuration is the other one of the first configuration or the second configuration.

16. The assembly of claim 1, wherein the at least two needles are substantially parallel in a non-deployed configuration, and the at least two needles diverge from one another in a deployed configuration with an angle of divergence of at least 20°; wherein the non-deployed configuration is one of the first configuration or the second configuration and the deployed configuration is the other one of the first configuration or the second configuration.

17. An assembly for anchoring in tissue, the assembly comprising:
an anchor part, the anchor part comprising:
a support having a distal face and a proximal face opposite the distal face,
at least two needles, each having a tip end configured to engage tissue, a head end opposite the tip end, and a stem extending from the head end to the tip end, wherein the stem of each of the at least two needles is at least partially embedded in the support, such that the tip ends project from the distal face,
wherein the at least two needles are positionable in a first configuration, and
a biasing part configured to position the anchor part according to a second configuration differing from the first configuration in an orientation of the at least two needles relative to one another, wherein the biasing part comprises a holding device configured to hold the anchor part in the second configuration, and
a delivery member, wherein the biasing part comprises a recess arranged at a distal end of the delivery member, wherein the recess has an access opening at the distal end;
wherein the support comprises a resilient material, such that the support is deformable and acts as a pivot when the at least two needles change between the first configuration and the second configuration; and
wherein the support is configured to be deformed to a compressed shape in which the support positions the at least two needles in the second configuration, wherein the recess is configured to accommodate the support when deformed to the compressed shape, and wherein the support positions the at least two needles in the first configuration when released from the compressed shape to an uncompressed shape.

18. The assembly of claim 17, wherein the recess has a cross sectional size smaller than a corresponding size of the support.

19. The assembly of claim 17, wherein the head ends are embedded in the support.

20. An assembly for anchoring in tissue, the assembly comprising:
an anchor part, the anchor part comprising:
a support having a distal face and a proximal face opposite the distal face,
at least two needles, each having a tip end configured to engage tissue, a head end opposite the tip end, and a stem extending from the head end to the tip end, wherein the stem of each of the at least two needles is at least partially embedded in the support, such that the tip ends project from the distal face and the head ends project from the proximal face,
wherein the at least two needles are positionable in a first configuration; and
a biasing part configured to position the anchor part according to a second configuration differing from the first configuration in an orientation of the at least two needles relative to one another, wherein the biasing part is releasable from the anchor part;
wherein the biasing part comprises a holding device configured to hold the anchor part in the second configuration,
wherein the holding device is configured to enter into locking engagement with the at least two needles,
wherein the holding device is configured to engage with the head ends of the at least two needles to form a co-operating guide and slide,
wherein the guide is configured to engage the slide both in the first configuration and in the second configuration and the guide is configured to permit the at least two needles to transition between the first configuration and the second configuration in response to a twisting motion of the biasing part relative to the support, and
wherein the support comprises a resilient material, such that the support is deformable and acts as a pivot when the at least two needles change between the first configuration and the second configuration.

* * * * *